United States Patent [19]

Nagabhusan et al.

[11] Patent Number: 4,832,532

[45] Date of Patent: May 23, 1989

[54] APPARATUS FOR DETERMINING LIQUID/GAS INTERFACES

[75] Inventors: Senapati Nagabhusan, Dublin; Larry J. House; Ralph E. Beard, both of Columbus; John R. Myers, Arlington, all of Ohio

[73] Assignee: Battelle Memorial Institute, Columbus, Ohio

[21] Appl. No.: 54,642

[22] Filed: May 27, 1987

[51] Int. Cl.$^4$ .............................................. B63C 11/48
[52] U.S. Cl. .................................. 405/185; 367/141; 367/910; 114/312
[58] Field of Search ............... 405/185, 186, 188, 190, 405/191; 114/312; 367/141, 910

[56] References Cited

U.S. PATENT DOCUMENTS

| | | | |
|---|---|---|---|
| 3,434,443 | 3/1969 | Estabrook | 405/185 X |
| 3,626,703 | 12/1971 | Richburg | 405/191 |
| 4,010,619 | 3/1977 | Hightower et al. | 405/191 |
| 4,212,258 | 7/1980 | Collins | 114/312 |

Primary Examiner—David H. Corbin
Attorney, Agent, or Firm—Klaus H. Wiesman

[57] ABSTRACT

An apparatus for carrying by a diver while underwater that provides information useful for enabling the diver to expeditiously and safely work on submerged vessels without the danger of tapping into an explosive gas. The invention is particularly useful for finding liquid/gas boundary in a submerged vessel or the pressure of liquid or gas behind the wall of a vessel. A transmitting transducer provides a low frequency acoustic tone burst that is transmitted toward the hull of the ship. The reflected signal from the inner surface of the hull is received by a hydrophone and processed. Electronic circuit means, responsive to the received signal, processes the signal and computes the location of a liquid/gas interface or the presence of liquid or gas behind the hull. A display provides indications of the computed values.

5 Claims, 5 Drawing Sheets

APPARATUS FOR DETERMINING LIQUID/GAS INTERFACES

STATEMENT OF GOVERNMENT INTEREST

The U.S. Government has rights in this invention as pursuant to Contract No. N00014-84-C-0360 between the U.S. Navy and Battelle Memorial Institute.

FIELD OF THE INVENTION

This invention describes a method and an apparatus for locating the boundary between a liquid and gas. The invention is particularly useful for finding the liquid/gas boundary inside an underwater vessel. There are many sunken vessels in the sea that contain unknown amounts of oil, fuel, or other noxious liquids that pose an environmental and navigation hazard. Some vessels are leaking these fluids or have the potential for leaking. If the vessel is to be pumped out, it is vital to know the liquid level inside in order to avert the dangers associated with tapping into an explosive gas.

BACKGROUND OF THE INVENTION

Many sunken vessels throughout the world contain unknown amounts of oil, fuel, or other noxious liquids that pose a hazard to navigation and to the environment. Some of the sunken vessels are leaking these fluids, and others have the potential to start leaking at any time. A salvage operator needs to have the capability to determine how much liquid or gas is in a particular sunken vessel and thus to be able to make informed decisions as to its disposition. If the sunken ship must be pumped out, it is important that salvage divers know the location of any liquid/gas interface. By knowing the liquid/gas interface location, divers can avoid the dangers associated with tapping into a potentially explosive gas.

Various methods of detecting liquid/gas interfaces through a ship's hull have been investigated. These methods, which have met with limited success, have included using fish finders (echo sounders) that rely on a sonic pulse-echo to penetrate the hull of a sunken vessel and reveal the nature of its contents. Unless the hull and tanks are geometrically simple in shape and construction, the data from these types of echo sounders are difficult to interpret and are not reliable.

U.S. Pat. No. 4,403,508 to Langlois relates to a soundwave method and device for locating interfaces in vertically-layered materials and determining concentrations in mixed materials utilizing acoustic impedance measurements. A high energy ultrasonic pulse is used. U.S. Pat. No. 4,203,324 to Baumoel discloses a sonic liquid level detector. Sonic pulses are reflected between the sides of a vessel containing the liquid. U.S. Pat. No. 4,144,517 to Baumoel reveals a single transducer liquid level detector. Decay rate of reflected sonic signals is an indication of the material on the other side of the plate. U.S. Pat. No. 3,019,650 to Worswick shows an apparatus for detecting the presence or absence of a body of liquid at a location. A transducer is coupled to the wall of the vessel. U.S. Pat. No. 2,990,543 to Rod discloses an earlier patent relating to the sensing of the presence or absence of material using "sonic" and ultrasonic transmission. These prior art systems are not satisfactory as liquid/gas level detectors because of difficulty in interpreting the output signals in ships and in use as self-contained units for undersea diver operation.

It is an object of this invention to increase the reliability and ease of making liquid/gas interface determinations in sunken vessels.

It is an object of the invention to provide a self-contained liquid/gas interface detector system capable of undersea operation.

It is a further object of the invention to provide a liquid/gas interface detector the sensitivity of which is not affected by thick steel plates (ship hull), marine growth, or transducer misalignment.

BRIEF SUMMARY OF THE INVENTION

This invention is based on the judicious choice of the principle of operation and the acoustic frequency band. At conventional sonar frequencies of 20 KHz to 100 KHz the reflectivity of steel/water interface and steel/air interface is about 98 percent or 100 percent respectively. Therefore it is impractical to reliably differentiate these two interfaces. This is because the acoustic impedance mismatch between steel and water and steel and air are both very large and therefore yield a small change in reflectivity. Also selecting a frequency for which the steel wall would be a quarter wave plate is not effective because of the high frequencies required and the precise orientation and alignment requirements for the transmitting and receiving transducer. However, if a low frequency tone burst at 100 Hz to 5 KHz is used, the affect of the steel wall on reflectivity can be practically eliminated. Therefore, the reflectivity measurement exhibits the large difference one would expect but uses a water/water interface and a water/gas interface. Thus, for water/steel/water the reflectivity is only 3 percent compared to almost 100 percent reflectivity for water/steel/gas interfaces. Furthermore, at these frequencies, the sound beam, is less attenuated in marine growths and has been demonstrated to penetrate normal marine growth on ship hulls without significant loss in signal. The apparatus of the invention has been successfully tested both in the laboratory and in the field.

Figure 3:
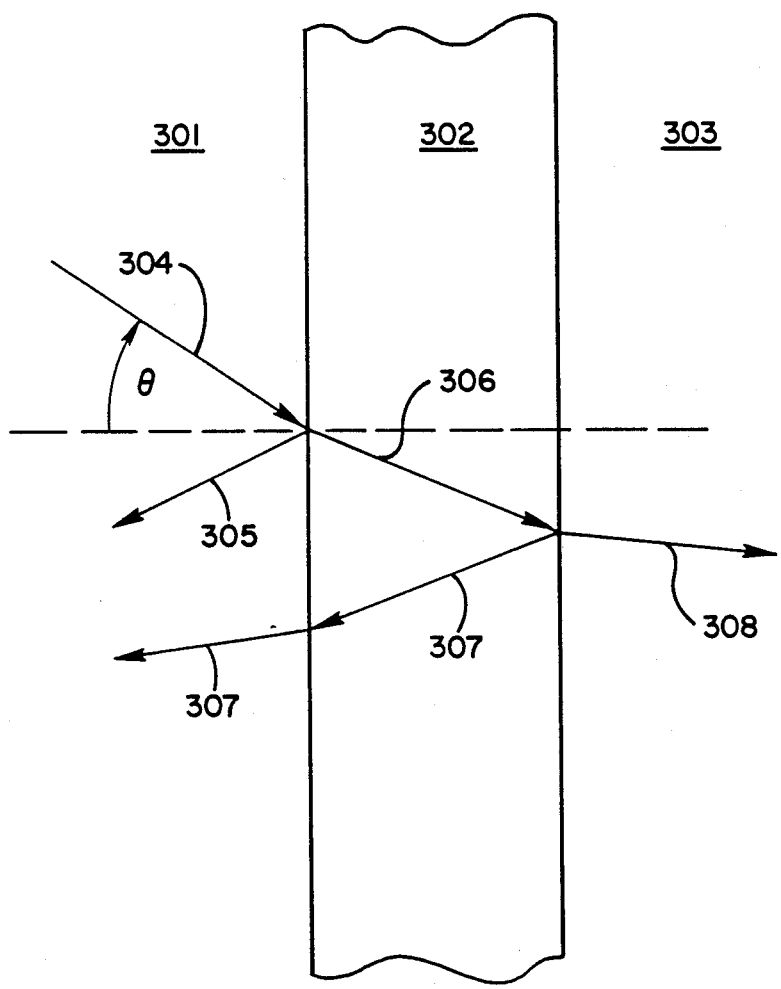
FIG. 3 is a schematic illustration of the path of the sonic beams that are produced by the apparatus of the invention.

An acoustic transmitting transducer generates an acoustic tone burst of the proper frequency which propagates through water to impinge on a vessel wall. If there is air in the vessel the acoustic burst is reflected back to the acoustic receiving transducer. If there is water in the vessel, a portion of the acoustic signal is transmitted into the water, so that the strength of the reflected acoustic signal decreases, as shown in FIG. 3. The amplitude of the received signal, therefore, is a function of the position of the transducer with respect to the water/gas boundary inside the vessel. The receiving transducer is surrounded by a cylindrical shield of syntactic foam to prevent direct acoustic coupling from the transmitter to the receiver. The angles of the transmitter and/or the receiver are not critical and may be as much as 10 degrees from the normal, relative to the vessel wall. However, this angle should not exceed 14 degrees, which is the critical angle of reflectivity between water and steel.

The device can also accurately measure liquid levels at an angle up to 45 degrees relative to the vessel wall. The thickness and/or composition of the vessel wall is not critical, and may be as much as ¾ of an inch thick and composed of virtually any solid material. The measurement is also insensitive to heavy marine growth on the vessel exterior. The method of the invention is relatively insensitive to the interior geometry or to projections attached to the interior of the vessel. It is also insensitive to solid or liquid films or coatings on the interior of the vessel provided the coating is thinner than the wall thickness.

DETAILED DESCRIPTION OF THE INVENTION AND PREFERRED EMBODIMENTS

The Liquid Level Detector (Detector) is a sonic device designed to "see" through a sunken ship's hull and "find" the interface between a liquid and a gas. This self-contained, battery powered device has been developed to provide divers with a means of locating potentially dangerous gas pockets in a downed vessel prior to salvage operations.

The Liquid Level Detector (Detector) has been successfully tested in the laboratory for functional performance and ease of handling. It has further been tested on actual ships in an ocean water harbor environment.

Figure 1:
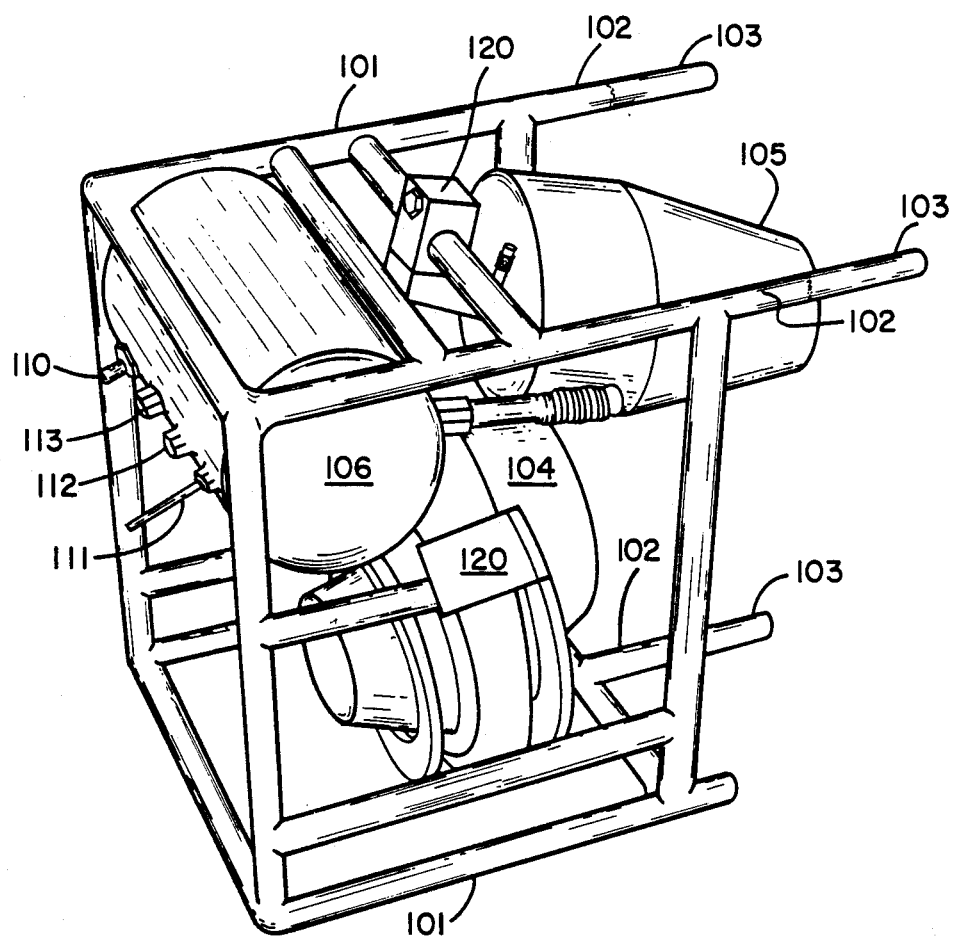
FIG. 1 shows an oblique view of the apparatus of the invention.
Figure 2:
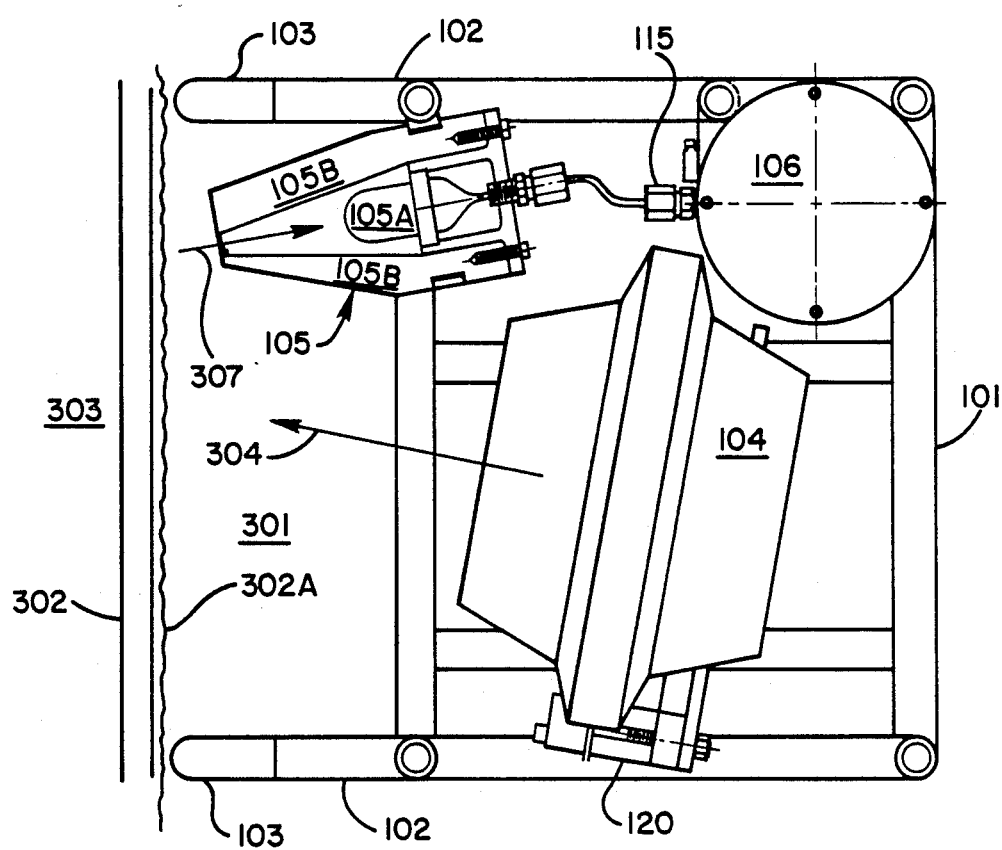
FIG. 2 shows a side view of the apparatus of the invention with the hydrophone portion cut away to show the inner arrangement of parts.

The Detector is illustrated in FIGS. 1 and 2. All components are located within a 37×33×25 centimeter framework of 1.9 centimeter O.D., 3 millimeter walled aluminum tubing. These dimensions are for illustration only and are not critical. The Detector 100 consists of a frame 101. The frame 101 has three projections 102 on the front to provide the proper standoff distance between a ship's hull and the sonic transducers. These projections 102 have replaceable tips 103 for changing the standoff distance according to the particular hull characteristics such as thickness, barnacle growth, paraffin coating, etc.

The large dish-shaped object inside the frame 101 is the underwater speaker or transmitting transducer 104. This device provides the acoustic signal that is transmitted through the ship's hull 302 and into the fluid 303 beyond. The signal frequency is on the order of 100 Hz to 5 KHz (Kilohertz). The signal is audible to the diver and is of moderate volume.

The smaller foam-covered device adjacent to the underwater speaker is the hydrophone receiver 105. This critical component receives the reflected acoustic signal for processing by the electronic circuitry. The hydrophone receiver is directional in that it concentrates its reception at a certain point. The foam shroud 105B assists the hydrophone 105A in this task by blocking acoustic waves from all but the desired (reflection) direction. The foam particularly inhibits the direct transmission of sound from the transducer 104 to the hydrophone 105A.

In the rear portion of the frame 101 is the cylindrical, aluminum, electronics housing 106. This housing is a pressure vessel, designed to operate below water at the required depths, and provides a dry, environment for the power amplifier and the signal processing circuitry. The housing 106 also contains the batteries 116, operating controls 110, 111 and indicators 112, 113. The controls consist of an on/off switch 110, a threshold adjustment 111, a green power indicator 112 and a red interface indicator 113. A detailed electrical schematic is shown in FIG. 4.

The aluminum frame 101, electronic housing 106 and other aluminum surfaces are preferably hard-coat anodized for corrosion protection. Both transducers are preferably mounted to the frame with vibration isolation pads 120 to prevent acoustic feedback through the frame 101. Electrical cables are fed through the electronics housing 106 by D. G. O'Brien underwater connectors 115.

FIG. 3 depicts the action of the incident, transmitted and reflected waves at a ship hull 302. Water or seawater 301 is in contact with a metal hull 302 that is in contact with an inner fluid 30 that may be water, oil, or gas. An incident wave 304 comes in contact with the hull 302 at an angle $\theta$. A first reflected wave 305 and transmitted wave 306 are formed. When the wave 306 contacts the inner hull surface a second reflected 307 and a transmitted wave 308 are formed. The effect of frequency on the reflected wave 307 and transmitted wave 308 is discussed below. Wave 307 is that wave received at the hydrophone and used to determine the material behind the hull 302.

Figure 4:
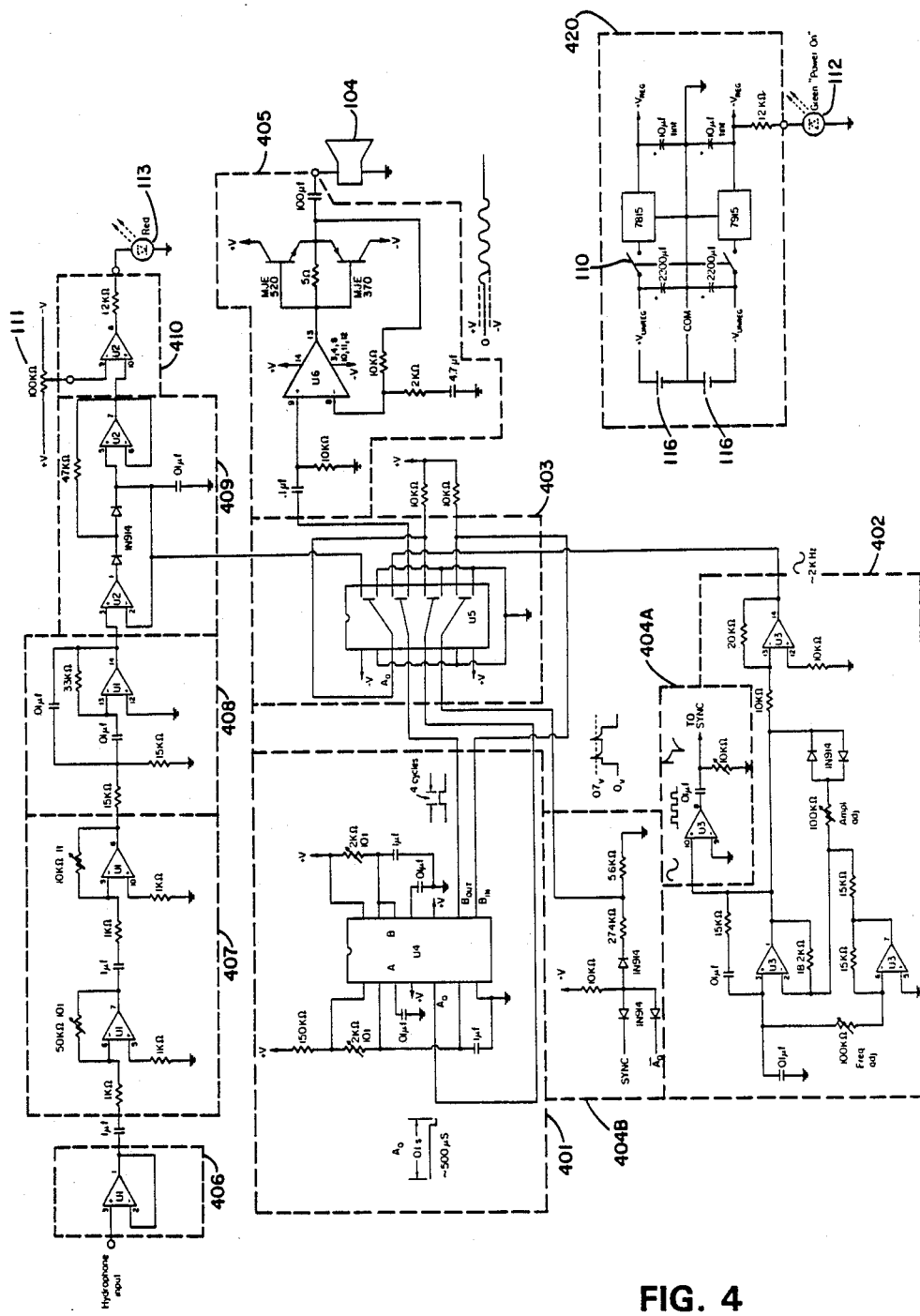
FIG. 4 illustrates in schematic form the general electrical connections of the invention.

Referring now to FIG. 4 the general schematic for the present invention is shown incorporating a presently preferred embodiment. The transmitting transducer 104 requires a 5 cycle, 2 KHz, C-W burst every 0.1 second to produce the desired acoustical signal. A switching pulse generator 401 drives a clock at 10 Hz to generate the burst envelope for the 2 KHz signal. A sine wave oscillator 402 produces the 2 KHz continuous signal which is gated by the switching pulse generator 401 and switch network 403 to produce the required 2 KHz signal.

The sync pulse generator 404A and conditioner 404B synchronizes the initiation of another signal burst with the reception of the signal received from the previous burst. The power amplifier 405 increases the strength of the burst signal and matches the output impedance of the circuit to the input impedance of the output transducer 104.

The hydrophone (receiving transducer) 105A accepts the reflected acoustic signals from the hull 307 and produces an electrical signal proportional to the reflected acoustic signal strength. This signal is buffered to the variable gain amplifiers 407 by the input buffer 406 which matches the hydrophone impedance to the amplifier 407 impedance. A bandpass filter 408 removes extraneous source signals. A full wave rectifier 409 eliminates the negative amplitude signal components. A level comparator 410, when enabled by the switching network, compares the peak signal amplitude to a preset level to excite the indicator light 113 whenever the signal exceeds the preset amplitude.

Power is provided by power supply 420 that generates the required regulated positive and negative voltage required. Batteries 116 supply the initial unregulated power.

The microcircuits used in the electrical circuits are shown in FIG. 4 and include:

| | | |
|---|---|---|
| Motorola | U1 | TL064 Quad. (MOS. Op. Amp.) |
| Motorola | U2 | TL064 Quad. (MOS. Op. Amp.) |
| Motorola | U3 | TL064 Quad. (MOS. Op. Amp.) |
| Motorola | U4 | XR556 Dual Timer I.C. |
| Motorola | U5 | AD7590D1 Quad. Analog. Switch |
| | U6 | APEX PA12 Power Op. Amp. |
| 7815, 7915 Voltage Regulators | | |
| MJE 370, MJE 520 Power Amplifiers | | |

In the method of the invention that depends on the measurement of hull plate reflectivity, much lower frequencies are used than in other techniques. This effectively eliminates the sensitivity to interface conditions and to intermediate layers. Also, since the technique operates at sufficiently low frequencies, the hull plate can be made essentially transparent. Thus, the reflection coefficient will change from a value near 1.0 when a gas is present on the inside of the vessel to a value of less than 0.1 at 1 KHz when a liquid is present: A change in reflectivity of nearly 90 percent at 1 KHz. This change in reflectivity contrasts with a change of only 5 percent for other techniques where the frequencies are much higher.

In the method of the invention the hull was treated as a semi-infinite plate immersed in an infinite fluid. A computer model used in the theoretical analysis assumed the propagation of plane compression waves and calculated the reflection and transmission coefficients as a function of hull plate thickness, transducer orientation, and frequency. The results of these calculations are shown in Table I for a steel plate with seawater on both sides (water/steel/water) and for a steel plate with seawater on one side and air on the other side (water/steel/air).

Figure 6:
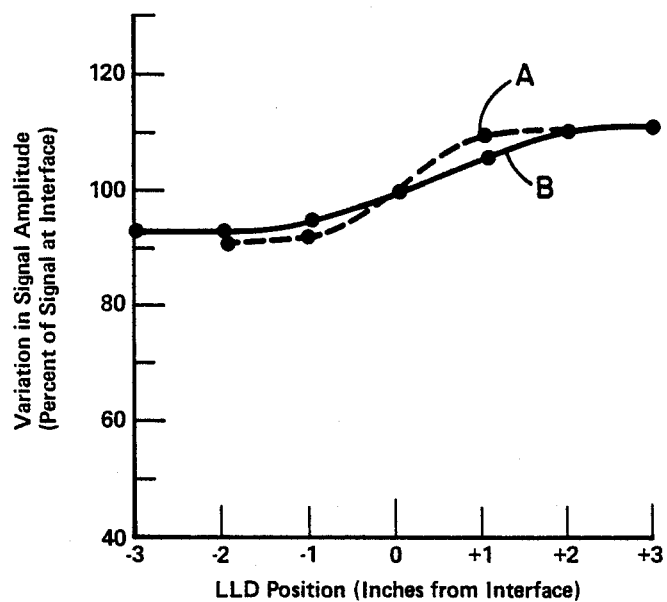
FIG. 6 illustrates in graphic form the variation in signal amplitude as a function of distance from the liquid level (along the hull). Dashed line A is for a beam at normal incidence and solid line B is for a beam at 45 degrees incidence.

The angle of incidence $\theta$ was found to have an insignificant impact on output for 0–10 degrees with respect to the normal to the surface of the steel plate or hull. At these lower frequencies, the effect of a small misalignment of the transmitter with respect to the hull did not produce any significant change in the reflection coefficient. This is important because it eliminates the need for a complicated underwater alignment procedure. However, the greater the angle $\theta$ the lower the sensitivity of the Detector. This is illustrated in FIG. 6 where the angle of incidence was 45 degrees.

Table I illustrates the large differences between the reflection and transmission coefficients for water/steel/water and these coefficients for water/steel/air below 20 KHz. These coefficients differ by more than 50 percent for frequencies below 6 KHz. It was found that for frequencies up to about 200 KHz the reflection and transmission coefficients for water/steel/air are independent of frequency, whereas the reflection and transmission coefficients for water/steel/water over the same frequency range depend on frequency.

The reflection of ultrasonic waves propagating at lower frequencies, unlike the reflection at higher frequencies, are not significantly affected by the layer of marine growth 302A on the hull 302 of a submerged vessel. In other words, the differences between the reflection coefficient for water/steel/water and the coefficient for water/steel/air measured in the frequency range of 100 Hz–5 KHz is sufficiently large that the effect of scattering produced by barnacles and other marine growth is negligible. The technique can thus be applied without having to clean the hull surface.

Tests showed that at lower frequencies below 6 KHz the water/metal(steel)/liquid(water) interface was essentially transparent to acoustic waves and transmitted them to the inner liquid while a water/metal(steel)/air interface reflected the acoustic waves. This is illustrated in Table I.

The data in Table I indicates that the upper threshold frequency of operation is below about 10 KHz to allow adequate discrimination of the signal although operation at a frequency below the crossover point at 5 KHz is preferred. Another factor that limits the lower frequency usable must also be considered. This factor is the fact that as the frequency is reduced wavelength increases and the ability to locate the liquid/gas boundary with precision is reduced. The width of the beam projected by the transducer 104 increases and resolution decreases. While lower frequencies down to 100 Hz are usable frequencies above about 500 Hz are preferred. In general, for increased resolution the ideal wavelength used in the Detector is about equal to or greater than ten times the thickness of the hull expected to be encountered. For greatest accuracy and reliability the ideal preferred frequency range is from 1–2 KHz. Tests for all of the Examples and Figures were performed at a frequency of 1–2 KHz.

TABLE I

| | Transmission/Reflection of Acoustic Waves Across a Boundary | | | |
|---|---|---|---|---|
| | Water | | Air | |
| Frequency (Hertz) | Percent Transmission | Percent Reflection | Percent Transmission | Percent Reflection |
| 1,000 | 98 | 2 | 5 | 95 |
| 2,000 | 90 | 10 | 4 | 96 |
| 3,000 | 81 | 19 | 3 | 97 |
| 4,000 | 71 | 29 | ≈2 | 98 |
| 5,000 | 39 | 61 | ≈1 | 99 |
| 6,000 | 48 | 52 | ≈1 | 99 |
| 7,000 | 45 | 55 | ≈1 | 99 |
| 10,000 | 28 | 72 | ≈1 | 99 |
| 20,000 | 9 | 91 | ≈1 | 99 |
| 30,000 | 4 | 96 | ≈1 | 99 |
| 40,000 | 2 | 98 | ≈1 | 99 |
| 100,000 | 1 | 99 | ≈1 | 99 |
| 200,000 | 1 | 99 | ≈1 | 99 |

EXAMPLE I

Tests were conducted in a laboratory tank containing a ½ inch-thick steel partition. This test verified that the received hydrophone signal amplitude changed with the water level behind the steel plate and that this signal change triggered a red indicator light just as the hydrophone crossed the water-air interface.

EXAMPLE II

To test the Detector under conditions more realistically representing its intended operational environment, tests were run in a diving pool. A 6-foot diameter, 6-foot-long cylindrical tank simulated a sunken vessel. This tank had one closed end and one open end, with the open end sitting on the pool floor and the closed end facing upward. A small hole had been drilled in the side of the tank about 18 inches from the top (closed end). The tank was filled with air until bubbles escaped from the drilled hole. This ensured that the air-water interface was precisely located. The pool contained fresh, chlorinated water maintained at 70 F. to 90 F. during all the tests.

To simulate various hull conditions, the tank was coated at different locations with several materials. In the initial testing location, there was no coating except for heavy oxidation. In a second location, automotive undercoating was sprayed on the inside of the tank to simulate a petroleum slick: Two coats of undercoating were applied to an approximate thickness of 1/16 inch. At a third location, polyurethane foam was applied to the outside of the tank to simulate marine growth; this coating reached thicknesses of more than ½ inch. Later, paraffin wax was applied on the inside of the tank, directly behind the foam coating, to simulate petroleum deposits. In a fourth location, a 3×3 inch-piece of steel angle was welded vertically to simulate a structural member.

The testing procedure consisted of scanning the outer surface of the tank with the Detector to locate the air-water interface. A diver operated the Detector while a temporary umbilical ran from the Detector to the surface so that the hydrophone signal could be monitored on a oscilloscope.

The Detector was able to find the air-water interface consistently through all the coatings. A typical "run" would have the diver start at the bottom of the tank and proceed upward. When the Detector was from 18 inches to 6 inches from the interface, the red indicator light would start to blink. When the upper edge of the foam shroud (equivalent to the top edge of the Detector) was within 1 inch of the interface, the red light would fully light up (stop blinking).

From observations of the hydrophone signal on the oscilloscope, the received signal was measured as changing in peak amplitude by 25 to 40 percent as the Detector was moved from the water to the air portion of the tank during all the pool tests.

The Detector was easily handled in the pool and the indicator lamps were visible. The acoustic signal emitted from the Detector is audible to the diver and is of moderate volume.

To further simulate the actual environmental conditions that the Detector is to operate under, three more tests were conducted in the laboratory tank.

EXAMPLE III

Figure 5:
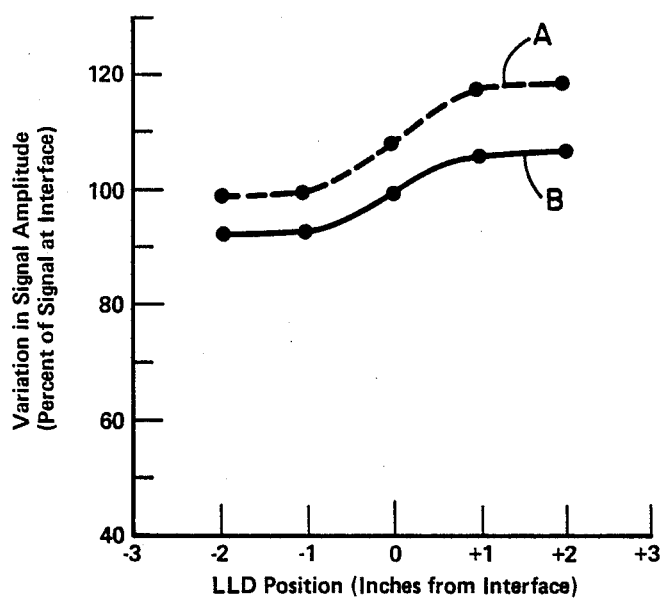
FIG. 5 shows a graph that depicts the variation in signal amplitude as a function of distance from the liquid level for two different thicknesses of steel plate. The dashed line (A) depicts the response for a ⅛ inch steel plate and the solid line (B) depicts the response for a ½ inch thick plate.

The effect of various hull thicknesses was tested by using two different steel plates: A ⅛ inch-thick plate and a ⅜ inch-thick plate. The received signal was monitored as the water level behind each plate was varied by submerging an air-filled plastic container immediately adjacent and behind each plate. Referring now to FIG. 5, the received signal was slightly larger for the thin plate than for the thick plate. However, the minimum received signal for the thin plate is still below the maximum received signal for the thick plate. This means that air can still be discriminated from water, but that the level behind the ½ inch-thick wall is erroneously detected about an inch lower than the same level detected through the ⅛ inch wall.

EXAMPLE IV

To simulate the effects of an angled hull (such as would be encountered near the bottom of a sunken vessel), a thin steel plate was mounted at a 45 degree angle with respect to horizontal inside the test tank. The received hydrophone signal was monitored as the water level behind the plate was varied by submerging an air-filled plastic container behind the plate. FIG. 6 shows the difference in signal strength with respect to the same test for an upright plate. Note that a 45 degree angle increases the "uncertainty region" from 2 to 4 inches. The effect of the misalignment is to flatten the response curve and reduce sensitivity. However, a misalignment of even 45 degrees does not adversely affect the operation of the Detector to the point where the result is not useful since drilling at the hull can be significantly below the interface.

EXAMPLE V

To simulate the effects of marine growth on performance, the thin plate in Example III was replaced by a ⅛ inch-thick steel plate containing moderate marine growth consisting primarily of barnacles and algae.

No difference in received signal strength could be detected between the two plates, indicating that the acoustic signal would not be affected by moderate marine growth on the face of the wall.

EXAMPLE VI

The Detector was taken to a Florida port facility for a performance test under actual conditions.

Two ships were inspected. The first was an old tanker ship with heavily corroded holds and a barnacled outer surface. One of the holds (tanks) was filled to a depth of 6 feet with seawater. The entire ship was then lowered in the water by filling other tanks until the surface of the test tank was 2 feet below the surface of the surrounding (dockside) water.

Two commercial divers operated the Detector. The divers were instructed in its proper use and were shown a videotape of the Detector being used in the research pool. The first diver then took the unit into the water. The diver used a hardhat breathing system and had surface communication gear.

The first diver required about a half hour to get used to operating the device, after which he could find the interface every time. The interface was detected repeatedly by moving the Detector up and down the hull vertically in both a clean region and a barnacled region. The Detector was also moved horizontally until it detected an adjacent empty tank. The Detector was run through these tests repeatedly and indicated air-seawater interfaces without fail. The hull of this ship ranged from ⅜ inch thick to ⅝ inch thick.

During all the tests in the dockside waters, the received signal from the hydrophone was monitored on an oscilloscope. Every time the Detector was placed in the dockside waters, a great deal of noise was displayed on the scope. The noise signal was so strong that the true signal could not be discerned at first, and the Detector was suspected of malfunctioning. The Detector was retrieved from the dockside water and was found to be ideal. It was assumed that there was a great deal of electrical interference in the local seawater and the Detector was returned to the diver. The scope was adjusted to emphasize the true signal over the noise, and this signal was photographed. The signal verified that the Detector was indeed working well and this was in turn verified by the diver.

The received acoustic signal increased by 65 percent due to the increased reflectivity from air behind the hull, compared with the reflectivity from water. This is significantly larger than the signal variation recorded in the laboratory or in the experimental pool. In the field, conditions more closely approximated the theoretical assumption of an infinite mass of gas behind the hull than did the experimental simulations.

A second ship was inspected by the second diver. This ship was a research vessel and was configured as a typical offshore supply boat. The tanks being inspected were wing tanks filled with number 2 diesel fuel. The hull was fairly clean, with some slimy vegetation present. The second diver was not told where the interface would be found, but he was able to locate it 3 feet below the surface within minutes of entering the water. These tanks were only about 3 feet wide, yet the Detector was not adversely affected by the back wall. The Detector was also taken down to the curved part of the hull until it was aimed 45 degrees with respect to vertical. The Detector still was not adversely affected; it performed as intended with the red lamp dark when oil was behind the hull and lit when gas was behind the hull. The Detector was also moved horizontally along the hull and was able to find an adjacent empty tank every time. The hull of this ship was about 0.4 inch thick.

Temperature tests revealed that a piezoelectric bimorph receiver originally used for the design was responsible for the sensitivity of the system to temperature fluctuations. Therefore, the receiver replaced with a commercial hydrophone that was less sensitive to temperature changes, was designed for use in seawater, was more rugged, and could be used at greater depths. FIG. 2 shows the details of the hydrophone receiver design. No vibration in sensitivity or signal strength as a function of water temperature was observed between 65 F. and 95 F. For temperatures outside this range electrical temperature compensation methods known in the art can be used to keep the unit stable. Specifically specifications for the receiving hydrophone are listed in Table II along with specifications for other major components.

TABLE II

| Component Specifications |
|---|
| Receiving Hydrophone: |
| Sensing element: lead zirconate titanate |
| Weight (dry): 2 pounds |
| Operating temperature range: −60 to 100 degrees Celsius |
| Maximum operating pressure: 3,000 psi |
| Sensitivity: −91 dB (reference 1 volt/microbar) |
| Frequency range: 0.1 to 10 KHz |
| Horizontal directivity: ±1 dB @ 20 KHz |
| Capacitance: 20,000 picofarads |
| D.C. Resistance: 1,000 megaohm (minimum) |
| Size: 1.75 inches maximum diameter × 5 inches long |
| Construction: polyurethane cable jacket, stainless steel sleeve and neoprene sheath |
| Vendor: Celesco Transducer Products Canoga Park, CA |
| Underwater Loudspeaker (transmitting transducer) |
| Weight (dry): 15 pounds |
| Maximum operating depth: 100 feet seawater |
| Resonant frequency: 1 KHz (nominal) |
| Construction: epoxy painted aluminum housing |
| Vendor: Lubell Labs Bexley, OH |
| Hydrophone Shroud: |
| Specific weight: 12 pounds/cubic foot |
| Crush pressure: 133 psi |
| Crush depth: 300 feet |
| Composition: polystyrene spheres in epoxy binder |
| Vendor: Emerson & Cuming Canton, MA |
| Frame and Electronics Housing: |
| Maximum operating depth: 100 feet |
| Construction: 6061-T6 aluminum, hard coat anodized |

Calibration of the Detector may be made on the surface by using a small tank having a container therein with a known liquid/gas interface or it may be made on a ship at the surface where a known bilge tank, fuel tank or other tank is adjacent to the hull.

Orientation of the hydrophone receiver 105 and the transmitter 104 relative to each other and the normal of the vessel wall to be inspected is determined empirically by adjusting the orientation of the receiver 105 and transmitter 104 until the reflected signal from the inner surface of the vessel wall is maximized. This can easily be done in a tank as part of the calibration procedure. These angles are then fixed and need not be changed.

Thicker hulls can be inspected by increasing the amplitude of the incident acoustic signal to compensate for the losses in the wall or the signal frequency can be decreased to permit more signal to pass through the hull wall. In an alternative embodiment two different burst frequencies are generated simultaneously and the received signals processed separately. This would make it possible to penetrate a thick hull while maintaining the high accuracy achievable with higher frequencies on the thinner hulls.

Another embodiment that would improve the accuracy, sensitivity, and reliability on both thick and thin hulls is the addition of an additional receiver added below the loudspeaker 104. The principle of operation is as follows: When the loudspeaker 104 crosses the interface, the received signal amplitude from the top hydrophone is greater than that from the bottom hydrophone. The difference between these two signals (called the "interface signal") would be largest when the device is directly over the interface and zero everywhere else. The sum of these two signals would be largest when the Detector is directly over air or gas, smallest when the Detector is directly over water, and intermediate when the Detector is near the interface. This embodiment decreases sensitivity to hull thickness and to other environmental factors.

A general device may be described as an apparatus for carrying by a diver while underwater and for providing information useful for enabling the diver to expeditiously and safely work on submerged vessels including transmitting transducer means providing an acoustical tone burst for projection toward a wall of the submerged vessel; a first electronic circuit means for providing a repetitive tone burst, to the transmitting transducer, where the tone burst is at a frequency in the range of 100 Hz to 5 KHz; a receiving transducer means for receiving an acoustic signal reflected from an inner wall of the submerged vessel and converting the signal to an electrical signal proportional to the received acoustic signal; a second electronic circuit means, responsive to the electrical signal from the receiving transducer, for processing the signal and computing the presence of a liquid/gas interface behind the wall of the vessel or the presence of liquid or gas behind the wall; and means for providing indications perceptible to the diver of the computed values.

A general method for determining the presence of a liquid/gas interface or the presence of a liquid or gas behind the hull of a submerged vessel includes generating and transmitting toward the vessel hull an acoustic tone burst at a frequency 100 Hz–5 KHz; detecting a reflected tone burst from the inner surface of the hull and converting the signal to an electrical signal proportional to the reflected tone burst; amplifying the electrical signal, comparing the signal to calibrated known values, and computing the presence of a liquid/gas interface behind the hull of the vessel or the presence of liquid or gas; and providing a display indicative of the computed values as to the conditions behind the hull.

While the forms of the invention herein disclosed constitute presently preferred embodiments, many others are possible. It is not intended herein to mention all of the possible equivalent forms or ramifications of the invention. It is to be understood that the terms used herein are merely descriptive rather than limiting, and that various changes may be made without departing from the spirit or scope of the invention.

We claim:

1. Apparatus for carrying by a diver while underwater and for providing information useful for enabling the diver to be expeditiously and safely work on submerged vessels comprising:
   a. transmitting transducer means providing an acoustical tone burst for projection toward a wall of the submerged vessel;
   b. a first electronic circuit means for providing a repetitive tone burst, to the transmitting transducer, where the tone burst is at a frequency in the range of 100 Hz to 5 KHz;
   c. a receiving transducer means for receiving an acoustic signal reflected from an inner wall of the submerged vessel and converting the signal to an electrical signal proportional to the received acoustic signal;
   d. a second electronic circuit means, responsive to the electrical signal from the receiving transducer, for processing the signal and computing the presence of a liquid/gas interface behind the wall of the vessel or the presence of liquid or gas behind the wall; and
   e. means for providing indications perceptible to the diver of the computed values.

2. The apparatus of claim 1, wherein the first electronic circuit means provides a tone burst at a frequency in the range of 500 Hz–2500 Hz.

3. The apparatus of claim 1, wherein the first electronic current means provides a tone burst at a frequency in the range 1–2 KHz.

4. The apparatus of claim 1, wherein the means for providing indications perceptible to the diver further comprises light output means.

5. The apparatus of claim 1, further comprising:
   a. frame means that provides rigid orientation of the transmitting transducer means relative to the receiving transducer means; and
   b. protective means disposed on the frame means that provides protection for the first and second electrical means while the apparatus is submerged.

* * * * *